United States Patent
Gunning

[11] Patent Number: 5,940,923
[45] Date of Patent: Aug. 24, 1999

[54] DENTAL IMPLANT CLEANING SYSTEM

[76] Inventor: Colleen K. Gunning, 3673 E. Phillips Cir., Littleton, Colo. 80122

[21] Appl. No.: 08/904,727

[22] Filed: Aug. 1, 1997

[51] Int. Cl.⁶ .............................. A46B 9/04; A61C 15/02; A61C 15/04
[52] U.S. Cl. ......................... 15/106; 15/167.1; 15/167.2; 15/172; 15/176.1; 15/176.5; 15/176.6; 132/309; 132/321; 132/323; 433/141
[58] Field of Search ......................... 15/105, 106, 167.1, 15/167.2, 176.1, 176.4–176.6, 172; 132/308–311, 321, 323; 433/141–143

[56] References Cited

U.S. PATENT DOCUMENTS

| | | | |
|---|---|---|---|
| 1,469,348 | 10/1923 | Wickberg | 15/176.1 |
| 1,897,365 | 2/1933 | Duey | 15/176.5 |
| 3,559,226 | 2/1971 | Burns | 15/167.1 |
| 3,720,975 | 3/1973 | Nelson | 15/167.1 |
| 3,994,039 | 11/1976 | Hadary | 15/167.1 X |
| 4,053,959 | 10/1977 | Wiley | 15/106 |
| 4,222,143 | 9/1980 | Tarrson et al. | 15/105 |
| 4,319,377 | 3/1982 | Tarrson et al. | 15/111 |
| 4,387,479 | 6/1983 | Kigyos | 15/167.1 |
| 4,449,934 | 5/1984 | Salam | 132/309 X |
| 4,534,081 | 8/1985 | Spademan | 433/142 X |
| 4,630,623 | 12/1986 | Hadary | 132/321 |
| 4,672,986 | 6/1987 | Hadary | 132/309 |
| 4,706,322 | 11/1987 | Nicolas | 15/106 |
| 4,942,894 | 7/1990 | Lai | 15/167.1 X |
| 5,067,195 | 11/1991 | Sussman | 15/167.1 |
| 5,499,420 | 3/1996 | Boland | 15/167.1 X |

FOREIGN PATENT DOCUMENTS

| | | | |
|---|---|---|---|
| 1044 | 3/1975 | European Pat. Off. | 15/167.1 |
| 2446617 | 9/1980 | France | 15/167.2 |
| 2951284 | 7/1981 | Germany | 15/167.1 |

*Primary Examiner*—Mark Spisich
*Attorney, Agent, or Firm*—Ruth Eure Biotechnology Patent Services

[57] ABSTRACT

The present invention provides an improved device for cleaning dental implant posts comprising a handle specifically adapted for ease of use by a person of limited or impaired dexterity or muscle control or a care giver and a series of brush and pick attachments specifically adapted for cleaning dental implant posts. This handle configuration eliminates the need for a pencil-like grip.

2 Claims, 2 Drawing Sheets

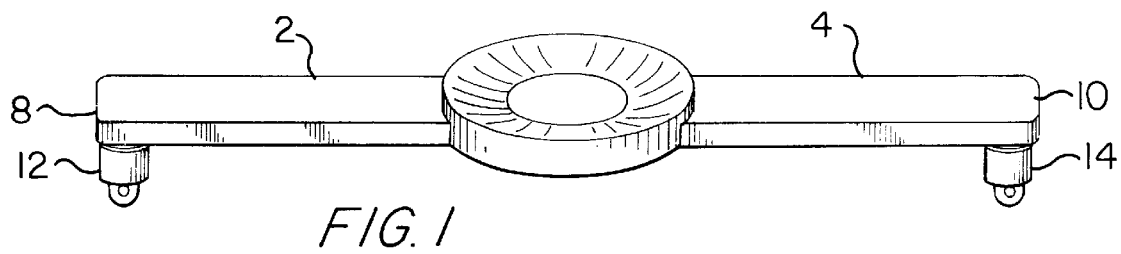
FIG. I
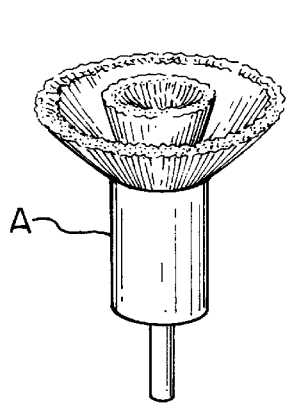
FIG. 2
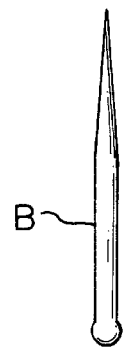
FIG. 3
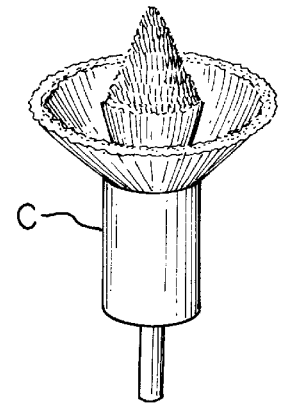
FIG. 4
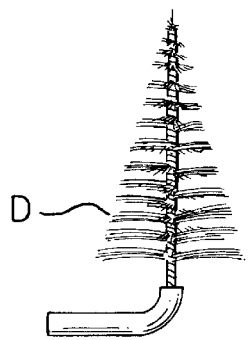
FIG. 5
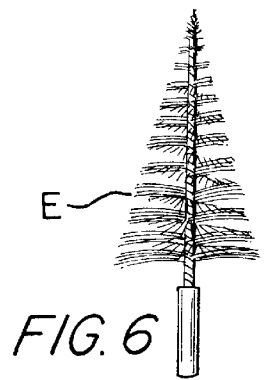
FIG. 6
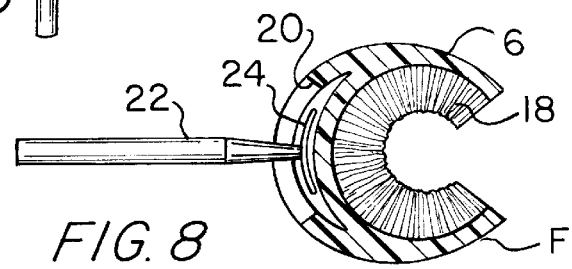
FIG. 7
FIG. 8

DENTAL IMPLANT CLEANING SYSTEM

FIELD OF THE INVENTION

The present invention relates to the field of dental implant post cleaning, and more specifically to an apparatus and method for such cleaning.

BACKGROUND OF THE INVENTION

Dental implants have become increasingly available and affordable to many and the use of such dental implants is generally more desirable than false teeth which are temporarily adhered to the gum surface.

Generally, surgery for such dental implants starts by making an incision in the gum of the patient to expose the bone and the implant is screwed into place. The implant is covered for three to six months to permit undisturbed healing. Thereafter, the top of the implant is exposed and a post is attached. A bridge is then secured onto the post and functions in the same manner as a natural tooth.

It will be appreciated that a portion of the post is generally accessible under the bridge. Thus, as with natural teeth, it is necessary to clean the bridge and post, particularly near and at the gum line. Thorough cleaning of these areas is required to prevent gingival infections around the implant posts, and to prevent plaque from building up in the gum crevice surrounding the in plant posts. It is this cleaning to which the present invention is directed. It will also be appreciated that many of the patients which benefit from dental implants are elderly and/or handicapped and require a device especially adapted for use by a person with limited dexterity. Some of the elderly and/or handicapped patients may require a device adapted for use by a care giver.

Heretofore, various types of tooth brushes have been adapted for this purpose. Examples of such tooth brushes adapted for cleaning interproximal and interdental areas are described in U.S. Pat. Nos. 3,559,226; 3,720,975; 3,939,520; 4,053,959; 4,222,143; 4,319,377, and 4,387,479. These references describe brushes having bristles radiating from a central shaft. As such, they are inadequate for cleaning a dental implant post. The requirements of effective dental implant post cleaning are met by the specifically adapted dental cleaning attachments of the present invention.

U.S. Pat. No. 5,067,195 describes a brush having plastic bristles held in place by twisted wire and bent to conform to a U-shape. The relationship of the handle to the brush described by the '195 patent is inadequate to meet the needs of a person with compromised dexterity or muscle control. Also, the wire spine of the brush would be likely damage a titanium dental implant post.

SUMMARY OF THE PRESENT INVENTION

It is an object of the present invention to provide an improved device for cleaning dental implant posts.

It is a further object of the present invention to provide an improved device for cleaning dental implants posts of a patient by a care giver.

It is a further object of the invention to provide an improved device for cleaning dental implant posts which allows a person of limited or impaired dexterity and muscle control to effectively clean his or her own dental implant posts.

It is an object of the present invention to provide an improved device for cleaning dental implant posts which has a permanently fixed brush or pick.

It is a further object of the present invention to provide an improved device for cleaning dental implants posts of a patient by a care giver which has a permanently fixed brush or pick.

It is a further object of the invention to provide an improved device for cleaning dental implant posts which allows a person of limited dexterity and muscle control to effectively clean his or her own dental implant posts which has a permanently fixed brush or pick.

It is an object of the present invention to provide an improved device for cleaning dental implant posts which has an interchangeable brush or pick.

It is a further object of the present invention to provide an improved device for cleaning dental implants posts of a patient by a care giver which has an interchangeable brush or pick.

It is a further object of the invention to provide an improved device for cleaning dental implant posts which allows a person of limited dexterity and muscle control to effectively clean his or her own dental implant posts which has an interchangeable brush or pick.

BRIEF DESCRIPTION OF THE DRAWINGS

FIG. 1 is side view of the handle of the present invention which is adapted for receiving an attachment.

FIG. 2 is a side view of attachment A.

FIG. 3 is a side view of attachment B.

FIG. 4 is a side view of attachment C.

FIG. 5 is a side view of attachment D.

FIG. 6 is a side view of attachment E.

FIG. 7 is a plan view of attachment F.

FIG. 8 is a top view of attachment F.

DETAILED DESCRIPTION OF THE INVENTION

Figure 10:
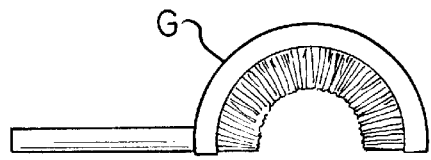
FIG. 10 is a side view of attachment G.

One embodiment of the present invention provides an improved device for cleaning dental implant posts comprising a handle specifically adapted for ease of use by a person of limited or impaired dexterity or muscle control or a care giver and a series of brush and pick attachments specifically adapted for cleaning dental implant posts. This handle configuration eliminates the need for a pencil-like grip.

Turning more specifically to FIG. 1, the handle of the device of the present invention comprises straight elongated end portions 2 and 4 projecting outward from the long axis of a central oval 180° from each other. The oval describes a flattened, slightly concave striated disk modified with radial indentations to form a finger grip for ease of grasping by a human hand. The oval portion can be any desired dimension which is suitable for grasping by a human hand, but dimensions of approximately about 3.5 to about 4.0 cm by about 2.5 to about 3.0 cm wide are also suitable. Mounted on the distal ends 8 and 10 are chucks 12 and 14 for receiving the shaft of an attachment. The attachments below described are mounted into the handle by inserting the shaft of the attachment into the chuck and turning the locking collar to firmly hold the attachment in the handle. Examples of attachments contemplated by the present invention are described below. Chucks 12 and 14 are mounted on the distal ends 8 and 10 of the handle such that the attachment is maintained in a fixed position perpendicular to the long axis of the handle.

FIG. 2 shows Attachment A which comprises a circular brush with radial disposed outward-flared bristles on its outer circumference surrounding a central brush. This attachment is used to clean and trace the gumlines, especially in areas of root concavities or depressions, as well as into the sulcus and under orthodontic brackets.

FIG. 3 shows attachment B which is a toothpick. This is used for stimulating and cleaning the interdental regions between the teeth. A plastic pick designed for use with this invention can be used, as well as a section of commonly available wooden toothpick. The length can be adjusted to accommodate the needs of the user.

FIG. 4 shows attachment C which comprises a brush having bristles graduated in length so as to form a point. This point is surrounded by a ring of radially disposed bristles. This attachment is used to trace the gumlines and work the point into any root concavities or furcations exposed by recession or gum surgery.

FIG. 5 shows Attachment D which is an interdental brush for cleaning in between the teeth. This attachment can be of a variety of geometric shapes, as well as of a variety of firmnesses of bristles. The firmness of bristles and geometric configuration can be suited to meet an individual's needs. Attachment D is shown in FIG. 5 as being an angle other than perpendicular to the axis of the handle. The shaft of this attachment is designed so the brush projects outwardly at an angle of about 60° to about 45° from perpendicular, as shown. This angle facilitates access to the interdental spaces, especially when wearing orthodontic hardware. This brush is designed to clean the interproximal areas under the archwires and between brackets.

FIG. 6 shows Attachment E which is also an interdental brush which can comprise a variety of geometries and firmness of bristles. The axis of the shaft of Attachment E is along the same axis as the brush, so that a perpendicular relationship of brush to handle is achieved, as shown in FIG. 6.

Attachments D and E described above are used by pushing the brush through the opened furcations and gingival embrasures or in and around orthodontic hardware and slightly against the surface of the tooth for cleaning in between the teeth.

Figure 9:
FIG. 9 is a side view of attachment F.

FIGS. 7, 8 and 9 show Attachment F which is particularly adapted for the cleaning of a dental implant post. The brush of this attachment describes an arc with inwardly directed bristles comprising brush 18 on the inside of the arc facing toward the center of the circle described by the arc. The portion of arc can be variable. A small portion of arc can be useful, but at least one half circle of arc up to a complete circle is contemplated by the present invention in order to circumscribe the dental implant post. FIGS. 7 and 8 depict an arc slightly greater than a half circle. Material suitable for such bristles could be similar to the hook material of hook and loop fastening means. Any other soft bristle material is suitable, however, since many implant posts are made of titanium, which is very soft. Metal wire bristle holders may be undesirable since metal contact may damage the post. This bristle material is mounted on the inside of a circular arc 6 or ring of plastic which is more rigid than the bristles in order to provide support for the bristles. The outside of the circular ring 6 contains a slot 20 which receives a disk 24. The disk 24 is attached to the end of shaft 22. The end of shaft 22 opposite the disk 24 fits into chuck 12 or 14. Disk 24 moves freely inside slot 20. When the handle is gently moved back and forth by the user, the disk 24 moves in the slot 20 which imparts a translational "rocking motion" to the brush 18 which cleans then entire circumference of a dental implant post in an effective and efficient manner. The translational motion from the gentle back and forth rocking of shaft 22 to the brush 18 facilitates adequate cleaning of a dental implant post by a user having limited or compromised dexterity or muscle control. The attachment is fitted onto the exposed dental implant post so that the bristles 18 are in contact with the dental implant post. The handle is moved back and forth so that the bristles 18 of the brush clean the entire circumference of the post. The bristles are moved against the implant post at various angles to access all exposed surfaces of the implant post to cleaning by bristles 18.

FIG. 10 shows Attachment G which is a crescent shaped hook with bristles on the inside of the crescent. Attachment G has no moving joint, as does Attachment F, described above, but is used in a similar fashion. An attachment held in a fixed position can receive greater force than an attachment having a movable joint.

Figure 11:
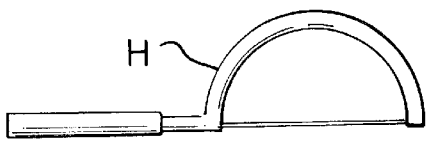
FIG. 11 is a side view of attachment HE.

FIG. 11 shows Attachment H which is a flosser attachment. This attachment facilitates flossing between teeth. The patient carefully pushes the floss into the interdental areas between the teeth with a vertical "see-saw" motion, then moves the floss against one surface of the tooth in an up and down motion. This floss is then moved against the surface of the adjacent tooth and the "see-saw" motion is repeated.

Figure 13:
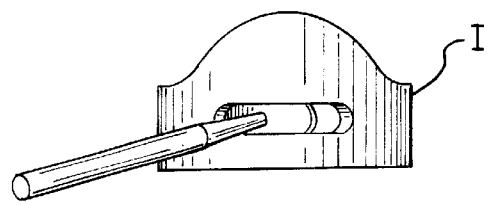
FIG. 13 is a back view of attachment I.
Figure 12:
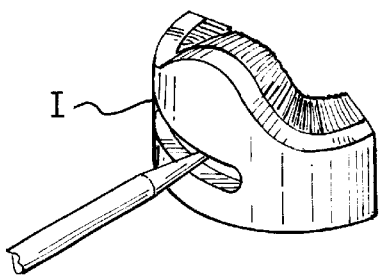
FIG. 12 is a plan view of attachment I.

FIGS. 12 and 13 show Attachment I which is a brush having a disk and slot for translational motion, as described for Attachment F. The brush of this attachment is designed to remove plaque from the face of a tooth with a gentle rocking motion of the shaft. This should be initially placed onto the tooth with the bristles pointing into the gumline. The brush is wiggled back and forth, up and down, following the curves of the tooth. This attachment can be disposable, for use in hospitals and institutions where cross-contamination is a consideration.

Figure 14:
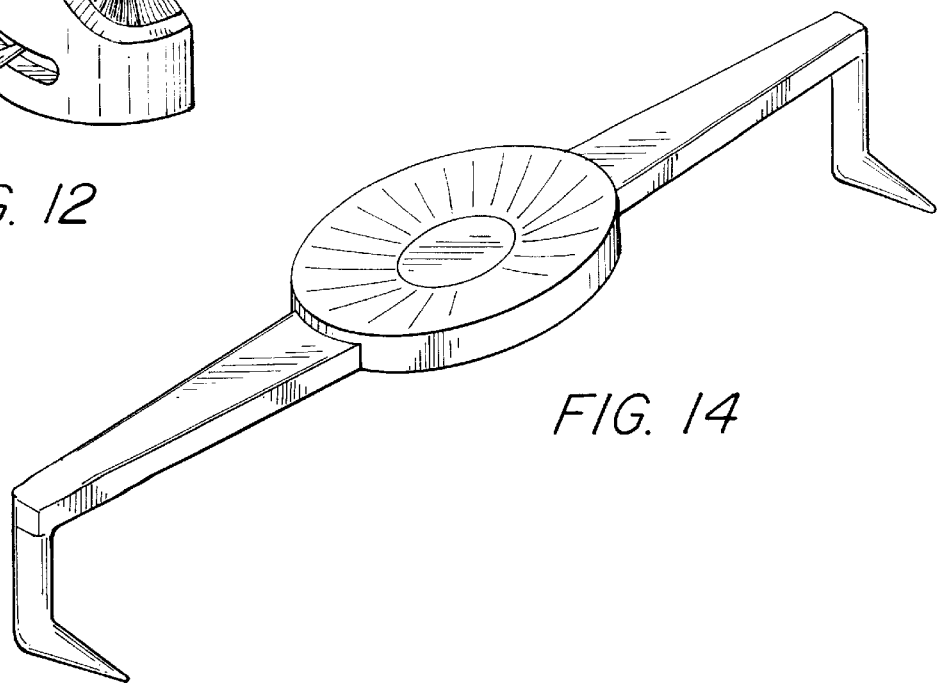
FIG. 14 is a side view of the device of the present invention having a permanently mounted brush or pick.

FIG. 14 shows the device of the present invention having a permanently mounted brush or pick mounted thereon. Any of the above-described attachments are envisioned as also being fixedly mounted to the handle.

It will be noted that although the above attachments are described with respect to a particular suggested method of use, it will be noted that each hygienist, dentist or user will have an individualized technique for performing a prescribed task. The methods of use described above are intended to be exemplary only, and are not intended to be in any way limiting the use of the attachments to the methods described.

The attachments described above and the handle, as well as the version describing the permanently fixed brush or pick may be made of material suitable for cleaning in a household dishwasher.

Various modifications and variations of the described invention will be apparent to those skilled in the art without departing from the scope and spirit of the invention. Although this invention has been described in connection with specific preferred embodiments, it is to be understood that the invention as claimed should not be unduly limited to such specific embodiments. Indeed, various modifications of the described modes for carrying out the invention which are obvious to those skilled in the art are intended to be within the scope of the following claims.

I claim:

1. A device for cleaning dental implant posts comprising:
   an elongated handle defining a longitudinal axis, said handle further having elongated end portions at opposite ends thereof, the elongated end portions being aligned with said longitudinal axis;
   a chuck located on a distal end of each of the elongated end portions, each of the chucks extending in a direction perpendicular to said longitudinal axis, each chuck including means for receiving a shaft portion of a cleaning attachment and a means for securing the shaft portion of the cleaning attachment therein; and
   a cleaning attachment comprising a shaft portion having a first end and a second end and a cleaning portion, wherein the shaft portion of the cleaning attachment is mountable within a selected one of the chucks, the cleaning attachment including means between the first end of the shaft portion and the cleaning portion for providing a sliding movement of the cleaning portion relative to the shaft portion, the sliding movement being along a substantially arcuate path and allowing the user to impart a rocking motion to the cleaning portion relative to the shaft portion.

2. The device of claim 1, wherein the means for providing sliding movement comprising a slot in a peripheral surface of the cleaning portion which is adapted to receive a disk mounted on the first end of the shaft portion which shaft portion is received at its second end into the selected one of the chucks.

* * * * *